United States Patent [19]
Wu

[11] Patent Number: 6,004,824
[45] Date of Patent: Dec. 21, 1999

[54] PROPOXYPHENE DERIVATIVES FOR IMMUNOASSAY REAGENTS

[75] Inventor: Robert Sundoro Wu, West Orange, N.J.

[73] Assignee: Roche Diagnostics Corporation, Indianapolis, Ind.

[21] Appl. No.: 08/886,800

[22] Filed: Jul. 2, 1997

Related U.S. Application Data

[63] Continuation-in-part of application No. 08/444,472, May 19, 1995, abandoned.

[51] Int. Cl.$^6$ .................. G01N 33/533; G01N 33/534; G01N 33/535; C07K 17/08
[52] U.S. Cl. .................. 436/533; 435/188; 436/544; 436/545; 436/546; 436/815; 530/405; 530/807
[58] Field of Search ............................ 435/188; 530/807, 530/405; 436/544, 545, 546, 533, 815

[56] References Cited

U.S. PATENT DOCUMENTS

| | | |
|---|---|---|
| 4,025,501 | 5/1977 | Leute . |
| 4,067,774 | 1/1978 | Rubenstein et al. . |
| 5,239,086 | 8/1993 | Dubler et al. .......................... 549/223 |
| 5,492,841 | 2/1996 | Craig ...................................... 436/534 |

FOREIGN PATENT DOCUMENTS

| | | |
|---|---|---|
| A-0 459 387 | 12/1991 | European Pat. Off. . |
| A-2 582 646 | 12/1986 | France . |
| WO A-93 03344 | 2/1993 | WIPO . |

OTHER PUBLICATIONS

Derwent Abstract No. AN 87–016372/03.
Frigola et al., Farmaco Ed. Sci., 43(4), 347–362, 1988.
McMahon et al., Life Sci., 12(10), Pt. 2, 463–473, 1973.

*Primary Examiner*—Mary E. Ceperley
*Attorney, Agent, or Firm*—Marilyn L. Amick; Roche Diagnostics Corporation

[57] ABSTRACT

The present invention provides hapten derivatives that are useful for the preparation of antigenic, antibody and label reagents having superior performance characteristics for use in immunoassays for the detection of d-propoxyphene and d-nor-propoxyphene. In the present invention the propoxyphene nucleus is derivatized out of the nitrogen center to form an aminoalkyl -carboxyl, or -hydroxyl haptenic derivative. The resulting hapten can then be further modified at the now functionalized position off the nitrogen for linking to an appropriate antigenic or labeling group to provide reagents for propoxyphene immunoassays having excellent sensitivity and selectivity for both d-propoxyphene and d-nor-propoxyphene.

11 Claims, No Drawings

PROPOXYPHENE DERIVATIVES FOR IMMUNOASSAY REAGENTS

This is a continuation-in-part application of U.S. Ser. No. 08/444,472, filed May 19, 1995, abandoned.

BACKGROUND OF THE INVENTION

1. Technical Field

The present invention relates to the field of immunoassays for the detection of dextropropoxyphene. d-Propoxyphene [(2S:3R)-4-dimethylamino-1,2-diphenyl-3-methyl-2-propionoxybutane] is a mild narcotic analgesic, and is present as the active ingredient of the drug, Darvon®. d-Propoxyphene is metabolized primarily via N-demethylation to d-nor-propoxyphene and further demethylated to d-dinor-propoxyphene. Urinary excretion in the 20 h urine following a 130 mg single oral dose of propoxyphene expressed as % dose were 1.1% propoxyphene, 13.2% nor-propoxyphene and 0.7% dinor-propoxyphene (RE McMahon et al,"The Metabolite Pattern of d-Propoxyphene in Man," *Life Sci* Vol 12, 463–473, 1973). The half-life of d-nor-propoxyphene in urine has been reported to be 22 hours(S. B. Karch, "The Pathology of Drug Abuse", CRC Press, 1993, Chapter 5, pp 269). It is desirable that immunoassays be developed that have the specificity to detect both d-propoxyphene and d-nor-propoxyphene in biological fluids, particularly human urine. Due to the resemblance of propoxyphene to methadone, it is also preferable that the assay not detect methadone.

2. Background

U.S. Pat. No. 4,025,501 discloses immunogens derived from carboxy modified propoxyphene haptens that are useful in eliciting propoxyphene-specific antibodies. The exemplified structure of the immunogen employed to make antibodies was a hemisuccinate ester. The resultingly formed immunogenic protein conjugates thus had the peptide residue leashed off the carboxy modified oxyphene chain.

U.S. Pat. No. 5,239,086 discloses haptens and tracers for immunoassays for d-propoxyphene and d-nor-propoxyphene. Here again, the disclosed compounds are made by leashing out of a derivatized oxyphene chain. Exemplary immunogen and labeled derivatives have the structures shown below:

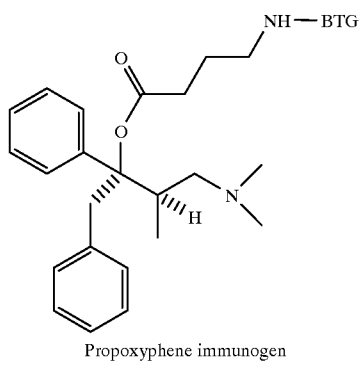

Propoxyphene immunogen

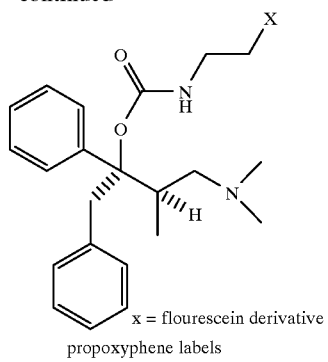

x = flourescein derivative propoxyphene labels

SUMMARY OF THE INVENTION

The present invention provides hapten derivatives that are useful for the preparation of antigenic, antibody and label reagents having superior performance characteristics for use in immunoassays for the detection of d-propoxyphene and d-nor-propoxyphene. In the present invention the propoxyphene nucleus is derivatized out of the nitrogen center to form an aminoalkyl a -carboxyl, or -hydroxyl haptenic derivative. The resulting hapten can then be further modified at the now functionalized position off the nitrogen for linking to an appropriate antigenic or labeling group to provide reagents for propoxyphene immunoassays having excellent sensitivity and selectivity for both d-propoxyphene and d-nor-propoxyphene.

DETAILED DESCRIPTION OF THE INVENTION

The present invention provides compositions derived from propoxyphene of the formula:

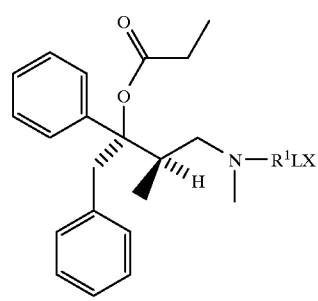

I wherein $R^1$ is a saturated or unsaturated straight or branched hydrocarbon of 1–15 carbon atoms;

L is a linker group through which X is bound and L is selected from the group consisting of —(C=O)$R^2$, —NH$R^2$, —N$R^1R^2$, and a linker group containing up to 15 carbon atoms and 5 heteroatoms, provided, however, that L does not contain sulfur;

X is a labeling group or an immunogenic carrier; and $R^2$ is a bond, —H or —OH.

As used herein, an immunogenetic carrier is a naturally occurring protein or polypeptide, such as BSA or BTG, or whole blood cell, bacterial cell, DNA or RNA.

To prepare the haptenic derivatives of the present invention it is preferable to utilize the nor-propoxyphene as the starting material. This material is commercially available but it is not economical. The synthesis of d-norpropoxyphene was reported albeit in a low yield [27%, from d-propoxyphene (J. Frigola et. al., Farmaco Ed. Sci, 43(4), 347–362, 1988)].

In a novel process for the preparation of the haptens of the present invention, demethylation of d-propoxyphene is accomplished using α-chloroethylchloroformate to form the urethane derivative followed by methanolysis to afford d-nor-propoxyphene hydrochloride in good (e.g. 47–59% ) yield. The d-nor-propoxyphene can then be derivatized at the nitrogen to a $C_{2-15}$ alkyl carboxyl, a $C_{2-15}$ alkyl amino, or a $C_{2-15}$ alkyl hydroxyl intermediate for the preparation of the compounds of Formula I.

A preferred process for the preparation of the carboxylated haptenic derivatives of the present invention involves reductive amination of d-nor-propoxyphene with an aldehyde having a useful group at the other end of the same molecule. Examples of these reagents are 4-carboxybenzaldehyde, 3-carboxybenzaldehyde, 4-nitrobenzaldehyde, 3-nitrobenzaldehyde and 2-nitrobenzaldehyde. The most preferred reagent for the reductive amination is the succinic semialdehyde. Reductive amination of d-nor-propoxypene in this manner provides the corresponding acid derivative in excellent yield.

An exemplary synthesis of an N-alkyl carboxylated haptenic derivative is illustrated in Scheme I below:

SCHEME I.

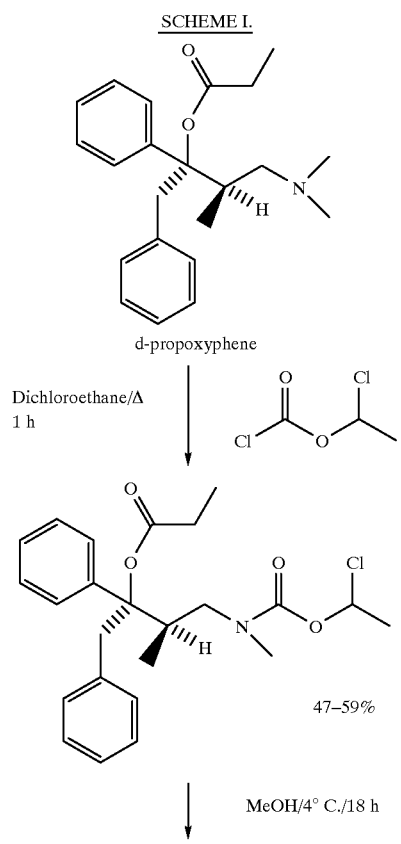

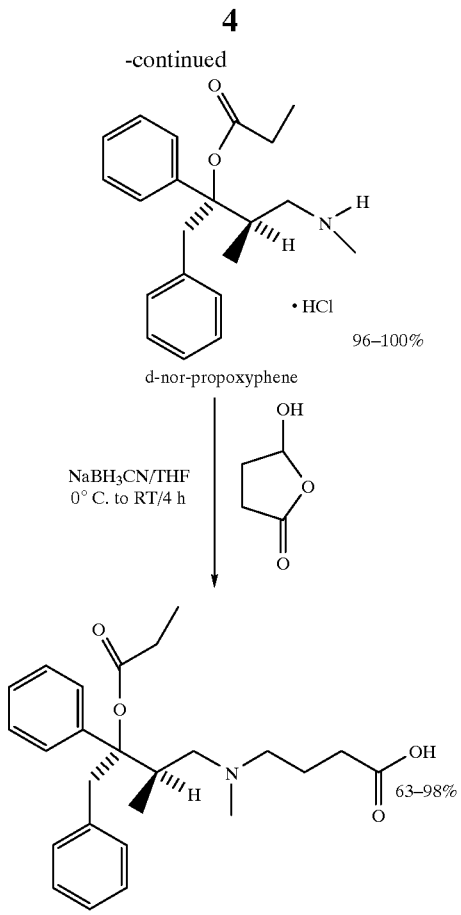

The d-nor-propoxyphene can also be alkylated with ethyl 4-bromobutyrate to provide the corresponding butyric acid ethyl ester and selectively hydrolyze further to give the hapten of the present invention. Other similar reagents can also be utilized to prepare the carboxylated propoxyphene hapten having an appropriate alkyl chain off the nitrogen position. Examples of such reagents are chloroacetic acid, and 6-bromohexanoic acid. For example, alkylation of nor-propoxyphene with chloroacetic acid in the presence of potassium carbonate in DMF can provide the acetyl linker arm at the nitrogen atom. This process of alkylation requires basic (pH) conditions. However, due to the lability of the d-nor-propoxyphene under such conditions (that is, the tendency of the molecule to undergo an N→O shift under basic conditions, see J. F. Nash, J. Pharm. Sci. 64:429, 1975 and J. W. King, Analyt. Toxicology 18:217–18, 1994), introduction of the linker may not proceed as expected or may result in a very low yield of the desired compound.

The d-nor-propoxyphene may also be aminoalkylated in order to prepare compounds of Formula I where L=—$NHR^2$ and —$NR^1R^2$. For example, nor-propoxyphene may be treated with formaldehyde in ammonium hydroxide to form aminomethyl derivative of nor-propoxyphene. Although this process alone is generally reversible, it lends itself to prepare directly the propoxyphene hapten conjugate by treating nor-propoxyphene with formaldehyde (or formalin) followed by the addition of lysine residues of proteins to the solution resulting in the formation of the desired immunogen containing an alkylamine bond (Mannich type reaction). This type of reaction will also allow introduction of an amino acid residue on the 1C leashed out of the nor-propoxyphene nitrogen atom.

A preferred method for introducing larger amino alkyl groups to the propoxyphene nitrogen is by reductive acylation. For example, a nitrophenyl substituted carboxylic acid such as 4(4-nitrophenyl)butyric acid can be reacted with the amine function of nor-propoxyphene to provide the corresponding amide. Hydroboration of the amide then affords the 4-nitrophenylbutyl derivative, this is followed by hydrogenation or reduction of the nitro compound to the corresponding amino derivative.

One method for the introduction of longer aminoalkyl sidechains on the nor-propoxyphene nitrogen group is by N-alkylation of the compound with haloalkylnitriles such as 6-bromohexanenitrile and more preferably with chloroacetonitrile. The resulting nitrites can be further reduced by methods known in the art to obtain the aliphatic aminohexyl derivative and the aminoethyl derivative of nor-propoxyphene. The amines are generally stored as the hydrochloride salts prior to use.

The above carboxy or amino functionalized derivatives can in turn be coupled to a variety of labeling groups or immunogenic carrier molecules by methods well known in the art to provide a variety of reagents useful in different assay formats. As used herein, a labeling group is a group or compound that is useful for detection, such as, a fluorophore (e.g., fluorescein), a radiolabel, or a chemilluminescent group. The hapten can be bound to microparticles including colored latex for use in spectrophotometric or direct optical detection formats such as latex agglutinographic or chromatographic strip tests. The label may also be an "indirect" label such as an energy transfer partner (energy donor or acceptor), enzyme or other group which is detected by further chemical reaction.

By attaching the hapten derivative of the present invention to a group consisting of an immunogenic carrier material, antisera and polyclonal antibodies, as well as monoclonal antibodies can be produced and isolated which are useful reagents for immunoassays for the detection of both d-propoxyphene and d-nor-propoxyphene. To prepare these immunogenic reagents, the hapten is covalently bound to the carrier material, usually a protein or peptidic residue such as, for example, BSA or BTG. Other suitable immunogenic carrier materials are set forth in U.S. Pat. No. 4,329,281 at Col. 2 and U.S. Pat. No. 5,101,015 at Col. 5. Additionally, these immunogenic carrier groups can be used to form non-immunogenic reagents, i.e., as tethers for the attachment of the haptens to solid matrices or labeling groups such as, for example, test strips, microparticles, radioactive labels, etc.

A wide variety of methods for covalently coupling the functionalized haptenic derivative to carrier materials is available in the art. A typical approach for the carboxy derivatives involves first further derivatizing the hapten at the hydroxyl with an activating group such as dicyclohexyl carbodimide or N-hydroxysuccinimide, and following with a relatively mild coupling reaction to the carrier. See also U.S. Pat. Nos. 5,101,015 at Col. 8 and 4,329,281 at Cols. 2–4.

Another suitable group for activating the carboxy haptenic derivatives is the thiazoline-2-thione. Other suitable active esters such as thioester, 4-nitrophenoxyester, 2,4-dinitrophenoxyester, pentafluorophenoxyester, mixed anhydride, azido and other leaving groups thereof described in Advance Organic Chemistry by March and in Principles of Peptide Synthesis by Bodanszky, Chapter II can also be used for the attachment of labeling groups, spacers or protein carriers. These methodologies are well known in the art.

In addition to carboxy activated derivatives, a wide variety of functional groups which allow covalent bonding with the labeling groups is known in the art. The selection of an appropriate functional group on the hapten depends on the nature of the functional group on the label that is chemically compatible for effective coupling. For example, a protein carrier that has ε-amino groups of the lysine residues of such protein can be linked to a hapten bearing an imidate ester group to form an amidine-linked conjugate. Haptens bearing an aldehyde group can be coupled directly to proteins bearing a hydrazide (which have previously been modified to contain a hydrazide functionality) to form a hydrazone bond. The same haptens bearing an aldehyde group can also be coupled to ε-amino groups of the lysine residues of protein to form an imine linkage which may be further stabilized by reduction to alkylamine bond with a suitable borohydride as such sodium cyanoborohydride as is exemplified by Brinkley (*Bioconjugate Chemistry*, Vol. 3, pp 2–13, 1992).

In addition, other amine-reactive modification reagents include, but not limited to, bifunctional cross-linking reagents as the homobifunctional linkers which are available through Pierce. These are disuccinimidyl suberate (DSS) as well as the water soluble analogs, sulfo-NHS ester and dimethyl suberimidate (DMS). (See Rebois, *Proc. Natl. Acad. Sci.*, Vol. 78, pp. 2086–2089).

Still other suitable amino activating agents for coupling include carbonyldiimidazole, phosgene, and 4-nitrophenylchoroformate. These agents allow conversion of the amine into an activated form for coupling to another amino-containing agent such as MoAb, enzymes, polymeric carriers such as aminodextran and polypeptides. For example, the use of phosgene or 4-nitrophenylchloroformate enables the conversion of the amino compound to the corresponding isocyanate which allows for coupling to another amine resulting in the formation of a urea-linked conjugate.

The hydroxy functionality lends itself to reaction with an isocyanate to form a carbamate, in order to prepare a carbamate-linked nor-propoxyphene derivative. To further exemplify this process, chlorosulfonyl isocyanate linker may be used and reacted with either N-hydroxyethyl nor-propoxyphene or N-(4-hydroxyphenyl propyl) nor-propoxyphene to form a carbamate-linked propoxyphene derivative in an activated form as the sulfonyl chloride. This activated group would then allow for coupling to another labeling group to form a 1:1 adduct (see U.S. Pat. No. 4,585,862).

In the case of either the attachment of labeling or immunogenic carrier group to the hapten derivative in accordance with the present invention, a linker group may optionally be incorporated between the $C_{1-15}$ alkyl functionality and the attached group. A wide variety of such linker groups may be provided between the hapten and label or immunogen to provide good exposure for antibody recognition. Generally, such linkage groups should not exceed 15 carbon atoms or contain more than 5 heteroatoms and may include various functionalities. As mentioned previously, the linker also should not include sulfur. Many such linker groups are incorporated between the hapten and the attached group directly as a result of the use of one of the functional coupling reagents described above. Alternatively, linkage moieties may be separately added to the functionalized amino terminus before adding the activated coupling group. The synthetic scheme for an amino methyl benzoyl linked hapten-protein (BSA) conjugate is illustrated in Scheme II below:

SCHEME II.
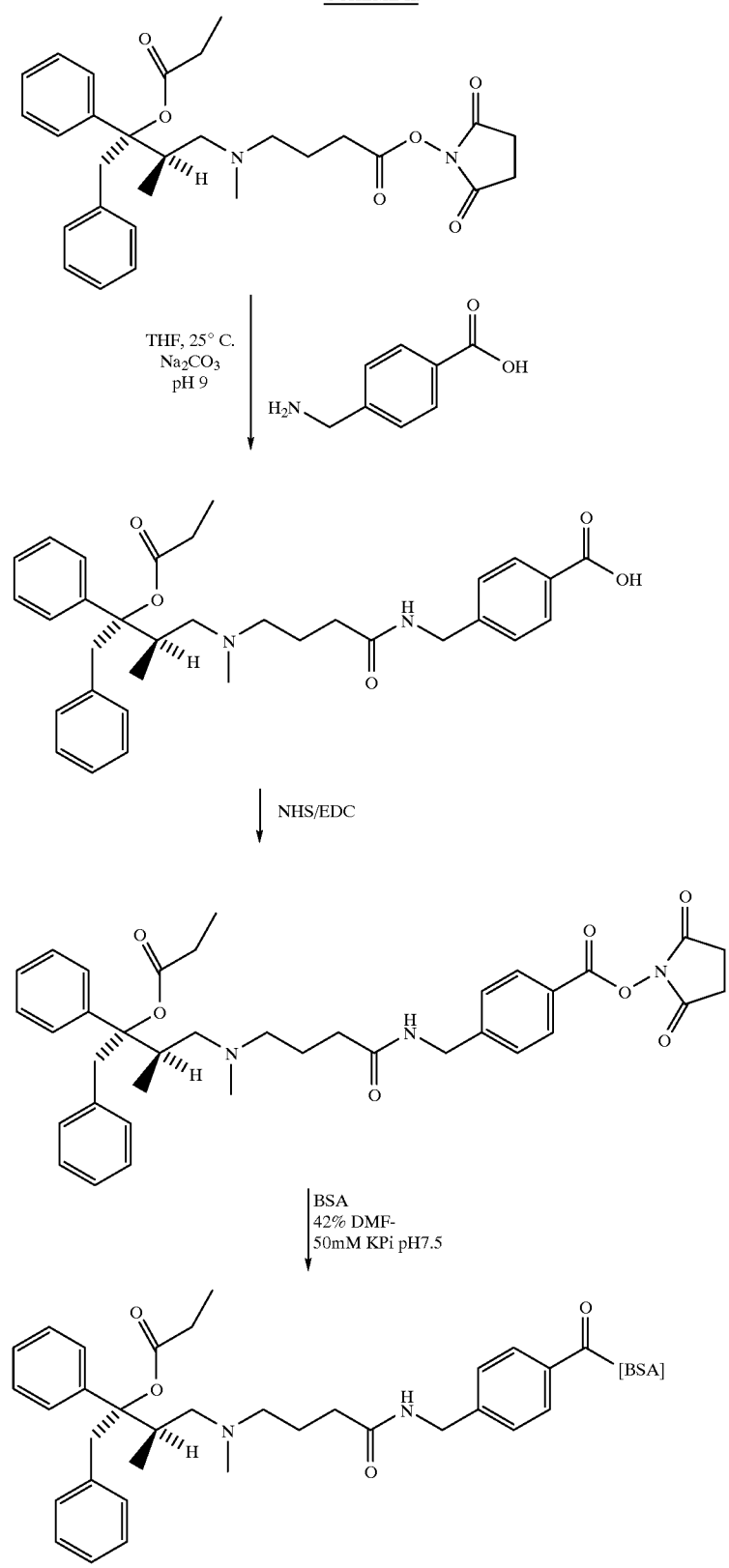

Still other linker groups can be employed as follows: diaminoalkane such as ethylene diamine, aminophenethylamine, amino acids other than cysteine, homocysteine, and small polypeptides of up to 15 carbon atoms and 5 heteroatoms (not including sulfur).

In a particularly preferred embodiment of the present invention for an agglutinographic immunoassay format, an immunogenic carrier composition as described above such as BSA is in turn bound to a microparticle utilizing the carrier as a tether between the microparticle and hapten portions. Typically, this reagent is prepared by first linking hapten to a protein having a plurality of active amino binding sites and in turn binding the protein at one or more remaining amino sites to latex microparticles having activated carboxyl binding sites. An amino methyl benzoyl linked protein conjugate such as the BSA derivative disclosed above bound to approximately 0.1 micron microparticles is a preferred example of such an embodiment.

The following Examples shall serve to further illustrate the embodiments of the present invention without intending in any way to limit the scope thereof.

EXAMPLE 1

Preparation of Propoxyphene Hapten

A. Preparation of [1S-(1R,2S)]-alpha-[2-[[1-chloroethoxy) carbonyl]]methylamino]-1-methylethyl]-alpha-phenyl benzeneethanol propanoate (epimers 1:1).

2.0 g (5.31 mmole) of propoxyphene hydrochloride was dissolved in 10 mL of water. This was treated with a sufficient amount of saturated $NaHCO_3$ until the solution turns basic. The mixture was extracted 2× with 25 mL portion of $CH_2Cl_2$ and dried over anhydrous $Na_2SO_4$. The solvent was evaporated to dryness to give 1.738 g (5.11 mmole) of a white cake. This was treated with 15 mL of dichloroethane to dissolve the material. After cooling under an ice-bath, the solution was treated with 0.565 g (5.62 mmole, 1.1 eq.) of α-chloroethyl chloroformate. This mixture was then heated to reflux for 1 h, cooled, followed by the removal of dichloroethane under reduced pressure to afford a yellow residue. The residue was chromatographed on a silica gel column of 2.5 cm×11 inches. Elution was carried out using a solvent mixture of EtOAc/Hexane (3:7). Fractions were collected. The major lower fraction(Rf ~0.37) was pooled while the minor upper fractions representing Rf~0.60 were discarded. Evaporation of the pooled fractions to dryness afforded 1.3 g of clear oil(59%). IR, NMR and MS were confirmatory.

B. Preparation of [S-(R,S)]-alpha-[1-methyl-2-(methylamino)-ethyl]-alpha-phenylbenzeneethanol propanoate hydrochloride.

780 mg (1.81 mmole) of the urethane prepared in A was dissolved in 10 mL of MeOH. The mixture was stirred overnight in a 4° C. cold box. MeOH was evaporated to dryness to give 667 mg (99+%) of white foam. Rf=0.45 (3:7 EtOAc/Hexane). IR, NMR and MS were confirmatory.

C. The preparation of [S-(R,S)]-4-[methyl[2-methyl-3-(1-oxopropoxy)-3,4-diphenylbutyl]amino]butanoic acid.

To a solution of 4.24 mL (0.69 g, 6.8 mmole, 15% solution in water, d1.09) of succinic semialdehyde in 15 mL of THF at 0–4° C. was added 1.89 mg (5.23 mmole) of d-nor-propoxyphene and 328 mg (5.23 mmole) of NaCNBH$_3$. The mixture was stirred for 2 h while allowing the reaction to reach room temperature. At this time a TLC sample revealed a complete disappearance of the starting material (Silica Gel, 85:15 $CH_2Cl_2$/MeOH). To this was added 15 mL of IN HCl and the reaction mixture was stirred for an additional 2 h. The reaction flask was then placed under reduced pressure to remove as much THF as possible. The remaining aqueous phase was treated with a sufficient amount of 1.0 N NaOH solution until the solution pH reaches 6–7. This was extracted 3× with ~20 mL portion of $CH_2Cl_2$. The combined organic layer was washed with 2×10 mL of saturated $NaHCO_3$ and 2×10 mL of $H_2O$, dried over anhydrous $Na_2SO_4$ and evaporated under reduced pressure to give 1.358 g (63%) of white solids with a good purity under TLC examination. Rf=0.37 (85:15 Ch2Cl2/MeOH). IR, NMR and MS were confirmatory of structure.

Note 1: The use of 1.1 equivalent of the succinicsemialdehyde is preferable or impurities at Rf=0.28 and Rf=0.67 were seen under TLC examination, 85:15 CH2Cl2/MeOH, ninhydrin.

Note 2: The yield improves as washing with $NaHCO_3$ was reduced to 1×. This gave a 98% yield of the material as white foam.

EXAMPLE 2

Preparation of Activated Ester Derivatives of Propoxyphene Hapten

Preparation of [S-(R,S)]-4-[methyl[2-methyl-3-(1-oxopropoxy)-3,4-diphenylbutyl]amino]-1-oxobutoxy]-2,5-pyrrolidinedione, 101 mg (0.225 mmole) of the butanoic acid hapten derivative from Example 1 was dissolved in 5 mL of dry $CH_2Cl_2$(freshly distilled over $CaH_2$). This was treated with 86 mg (0.45 mmole) of EDC and 51.7 mg (0.45 mmole) of N-hydroxysuccinmide. The reaction mixture was stirred for 18 h under atmospheric argon, then washed with 2×3 mL of 0.2N HCl, 2×5 mL of saturated $NaHCO_3$, 5 mL of dilute methanesulfonic acid. 2×5 mL of $H_2O$ and finally dried over anhydrous $Na_2SO_4$. The solvent was evaporated to dryness to afford 125 mg of white foam(92%). Structure was confirmed by IR, NMR and MS.

Note 1: Storage of the sulfonate salt for 1.5 mos in dessicator indicates no decomposition of the NHS ester.

Note 2: Under TLC examination, the fresh sample indicates the decomposition of NHS ester to the starting material.

Note 3: Omission of the methanesulfonic acid wash is recommended since the free base is also relatively stable(2 days).

EXAMPLE 3

Preparation of Activated Hapten with Linker Group

A. The preparation of [S-(R,S)-1-[[[4-[[4-[methyl[2-methyl-3-(1-oxopropoxy)-3,4-diphenylbutyl]amino]oxobutoxy]amino-methyl]benzoic acid.

A solution of 2.0 g (0.0132 mol) of 4-(aminomethyl) benzoic acid in 135 mL of tetrahydrofuran and 65 mL of $H_2O$ was treated with 5 mL of 1N NaOH solution to give a pH of about 9 or 10. Then added a solution of 6.7 g (0.0132 mol) of the ester of Example 2 in 135 mL of tetrahydrofuran and stirred at room temperature. Every 5 to 10 min. over the next hour added 2 or 3 mL of 1N NaOH solution to drive the reaction to completion. (This amounted to 25 mL of 1N NaOH solution). The reaction was then neutralized to pH 6.5 with 6N HCl, diluted with 500 mL of methylene chloride and washed with 250 mL of saturated brine solution. The aqueous layer was extracted with 250 mL of methylene chloride. The organic layers were combined and washed with 250 mL of 50 mM pH 8 potassium phosphate buffer solution, dried over anhydrous sodium sulfate and concentrated at reduced pressure to yield 6.7 g (93.5%) of white amorphous solid. NMR shows this to be about 85 to 90% pure and may be used without further purification. The above solid was chromatographed on 350 g of silica gel using 9:1 methylene chloride-methanol to remove front running impurities, then 75:25 methylene chloride-methanol to elute the product to yield 5.02 g (70.0%) of the benzoic acid as a white amorphous solid. IR, NMR and MS were confirmatory.

Note: The use of excessive silica gel will result in a poor recovery of the product. A ratio of 40:1 to 50:1 by weight of silica gel/compound is recommended.

B. Preparation of [S-(R,S)-1-[[[4-[[4-[methyl[2-methyl-3-(1-oxopropoxy)-3,4-diphenylbutyl]amino]-oxobutoxy] aminomethyl]-phenyl]carbonyl]oxy]-2,5-pyrrolidinedione. A round bottom flask was charged with 170 mg (0.31 mmole) of the benzoic acid from A. 119 mg (0.62 mmole) of EDC 71.3 mg (0.62 mmole) of N-hydroxysuccinimide and 6 mL of freshly distilled $CH_2Cl_2$. The reaction mixture was stirred overnight under an argon atmosphere. This was then washed with 2×5 mL of saturated sodium bicarbonate 2×5 mL of water and dried over anhydrous sodium sulfate. Solvent was removed under reduced pressure to afford 169 mg (85%) of white foam which indicated good purity by TLC Rf=0.33 (85:15 $CH_2Cl_2$/MeOH). 85 mg of this material was purified over a silica gel column(1.5 cm I.D.×18 cm length) and eluted with a mixture of solvent consisting of 85:15 $CH_2Cl_2$/absolute EtOH to yield 72 mg (85% recovery) of white foam. IR, NMR, MS results were consistent with structure.

EXAMPLE 4

Preparation of Propoxyphene-BTG Conjugate

Preparation of propoxyphene immunogen, [S-(R,S)]-4-[methyl[2-methyl-3-(1-oxopropoxy)-3,4-diphenylbutyl] amino]-1-oxobutyl-BTG. 92 mg (0.223 mmole) of the butanoic acid hapten derivative of Example 1 in 5 mL of anhydrous $CH_2Cl_2$ was treated with 51.2 mg (0.446 mmole) of N-hydroxysuccinimide and 85.6 mg (0.446 mmole) of EDC. The mixture was stirred under atmospheric argon at RT for 18 h. This was then washed with 2×5 mL of 0.1N HCl, 2×5 mL of sat. $NaHCO_3$ and 10 mL of $H_2O$. The organic layer was dried over anhydrous $Na_2SO_4$. The solvent was removed under reduced pressure to afford 99.8 mg (88%) of white foam. This material is redissolved in 1 mL of dry DMSO for protein coupling as described below. 650 mg ($9.7 \times 10^{-4}$ mmole, 18 mL of 36.2 mg/mL in 50 mM KPi pH=7.5) of BTG was cooled with an ice-bath and treated with 54 mL of DMSO added dropwise. After the temperature equilibrated to RT, 1 mL of DMSO-hapten solution prepared earlier was added dropwise. The reaction mixture was stirred for 18 h at ambient temperature and poured into a dialysis bag of 50 k cut-off. The bag was dialyzed using a stepdown gradient as follows:

1 liter of 75% DMSO in 50 mM KPi pH=7.5

2 liter of 50% DMSO in 50 mM KPi pH=7.5

2 liter of 30% DMSO in 50 mM KPi pH=7.5

2 liter of 15% DMSO in 50 mM KPi pH=7.5, and

4×2 liter of 50 mM KPi pH=7.5

The resulting conjugate was then filtered through a 0.22µ sterile filter to give 102 mL of the immunogen. The protein concentration is determined to be 5.6 mg/mL and the lysine modification is 93%. Total protein recovery=88%.

EXAMPLE 5

Preparation of Goat Antiserum

Animal Immunizations/protocols:

The propoxyphene-BTG conjugate of Example 4 is mixed 1:1 with Freunds adjuvant. Each goat received multiple site injections across the back as follows:

| 1st week | Complete Freund | 1.0 mg | Across back |
|---|---|---|---|
| 2nd week | Incomplete | 1.0 mg | Across back |
| 3rd week | Incomplete | 1.0 mg | Across back |
| 4th week | Incomplete | 1.0 mg | Across back |
| 8th week | Incomplete | 0.5 mg | Across back |
| Monthly | Incomplete | 0.5 mg | Across back |

EXAMPLE 6

Preparation of Microparticle Reagent for Agglutinographic Immunoassay

A. Preparation of propoxyphene-BSA conjugate 0.5–3 mg of the NHS ester from Example 3 was dissolved in 1 mL of dry DMSO (over molecular sieves) to make 1 mg/mL of hapten. This was set aside. 100 mg(1.47 µmole) of BSA was dissolved in 10 mL of 50 mM potassium phosphate buffer pH=7.5 and cooled with an ice bath. To this was added slowly 9 mL of DMSO. After the temperature was allowed to equilibrate to room temperature, 1 mL of the previously prepared hapten solution was added dropwise with stirring. Stirring was continued for 18 h at ambient temperature. The resulting conjugate was placed in a dialysis bag of 10 k cut-off. Dialysis was carried out in stepwise gradient of buffers with decreasing DMSO concentration. At the end of dialysis, the conjugate was filtered. The concentration BSA-hapten conjugate was determined by BioRad protein assay (Coomasie Blue). This conjugate may be stored frozen.

B. Preparation of Microparticle Reagent

Materials.

Carboxylated microparticle (0.09 to 1.2 micron.) N,N-dimethylformamide, 1-Hydroxybenzotriazole(NHB.H20). NHB.H20 in 2.5 mL DMF, then adding 2.5 mL of deionized water and mixing. The total volume is 5.0 mL at a concentration of 25 mg/mL. 1-Cyclohexyl-3-(2-morpholinoethyl) carbodiimide metho-p-toluene sulfonate (CMC). CMC stock solution is freshly prepared by dissolving 0.25 g in 5 mL H2O just before use, concentration=50 mg/mL). Triton X-100, propoxyphene-BSA conjugate. 50 mM sodium carbonate pH 8.6, BSA fraction V reagent grade. 10 mM potassium phosphate buffer pH 6.0 containing 0.1% sodium azide and 0.1% Triton X-100. Storage buffer: 0.01 M potassium phosphate buffer pH=6.0 containing 0.1% NaN3 and 0.1% Triton X-100.

Activation of Microparticle Reagent.

Ten mL of carboxy modified microparticle (10% solids) is washed by centrifugation with 0.1% Triton X-100 at a ratio of 1:1000,000 by volume to exchange the detergent. The microparticle concentration is adjusted to 3% by measuring of a standard curve at 500 nm. 33 mL of this, under rapid stirring, is added slowly with 2 mL of NHB stock solution. The suspension is stirred for 10 minutes at room temperature. 2.9 mL of the freshly prepared CMC stock solution is added dropwise. After addition of CMC, the microparticle suspension is stirred for 3 hr at room temperature, then washed with 0.1% Triton X-100 as above to remove the organic solvent and excess activating agents. The concentration of microparticle is adjusted to 2% solids(measured at 500 nm)

C. Coupling of propoxyphene-BSA conjugate to microparticle.

187.5 mg of BSA and 62.5 mg of the propoxyphene conjugate from A are dissolved in 50 mL of 50 mM sodium bicarbonate, pH 8.6. 50 mL of the activated microparticle is rapidly added under stirring at 25° C. The microparticle is washed by centrifugation with the storage buffer at 1,000,000 fold to remove the excess BSA. This reagent is adjusted to 10% solids using the storage buffer.

EXAMPLE 7

Microparticle Assay for Propoxyphene

Assay Reagents and Protocols, as performed on the automated COBAS MIRA, and MIRA-S configured at a 300 ng/mL cut-off. Kinetic interaction of microparticles in suspension yielding microparticle aggregation is measured for turbidity change. Changes in absorbance are measured.

1. Antibody reagent.

Goat antiserum in accordance with Example 5 is centrifuged at 8,000 rpm for minutes at 2–8° C. Supernatant is decanted and filtered through a Whatman Qualitative filter paper. The antiserum is diluted with 300 volume of antibody diluent. (antibody diluent: 50 mM Hepes pH6.5 containing 0.1% BSA, 0.5% sodium chloride, 0.5% dextran sulfate, 277 TIU/L of aprotinin, and 0.1% sodium.)

2. Microparticle reagent

Dilute the stock 10% microparticle in reaction buffer (10 mM potassium phosphate buffer pH=6.0 containing 0.1% sodium azide/0.1% Triton X-100) to give concentration of 0.7% solids.

3. Propoxyphene calibrator 0, 150, 300, 600 ng/mL of propoxyphene in human urine containing 0.05% sodium azide.

4. Reaction buffer.

50 mM Pipes pH7.0 containing 2.5% PVP, 2% sodium chloride, and 0.1% sodium azide.

Assay procedure for COBAS MIRA-S:

a. Sample: 10 mL b. Reacton buffer: 85 mL c. Antibody reagent: 100 mL d. Microparticle: 49 mL Mix sample with reaction buffer and antibody reagent and read background; Add microparticle reagent, incubate 30 seconds or a specified time according to the automated COBAS instrument and read absorbance at 500 nm.

The following data for a standard curve is obtained using the above described reagents, assay and using the propoxyphene calibrator as the sample.

| Reference Standard | O.D. (n = 5 Reps) | Avg. O.D. | (Accept O.D.) |
| --- | --- | --- | --- |
| 0 ng/mL | 1.692 | 1.692 | (>1.50) |
|  | 1.672 |  |  |
|  | 1.700 |  |  |
|  | 1.697 |  |  |
|  | 1.698 |  |  |
|  | 1.396 |  |  |
|  | 1.402 |  |  |
|  | 1.375 |  |  |
|  | 1.414 |  |  |
| 150 ng/mL | 1.440 | 1.405 |  |
|  | 1.138 |  |  |
|  | 1.167 |  |  |
|  | 1.140 |  |  |
|  | 1.126 |  |  |

| Reference Standard | O.D. (n = 5 Reps) | Avg. O.D. | (Accept O.D.) |
| --- | --- | --- | --- |
| 300 ng/mL | 1.165 | 1.147 |  |
|  | 0.967 |  |  |
|  | 0.965 |  |  |
|  | 0.955 |  |  |
|  | 0.967 |  |  |
| 600 ng/mL | 0.974 | 0.966 | (>0.90) |

Specificity

The following structurally related compounds were tested for cross-reactivity on three different COBAS MIRA instruments. The compounds tested were prepared in normal human urine. The results are expressed as that amount of each compound capable of giving a result equivalent to 300 ng/mL Propoxyphene.

| Compound | Approximate ng/mL Equivalent to 300 ng/mL Propoxyphene | Approximate Percent Cross Reactivity |
| --- | --- | --- |
| MIRA | | |
| Nor-propoxyphene | 390 | 77 |
| p-Hydroxypropoxyphene | 1,408 | 21 |
| Methadone | 1,034,500 | 0.03 |
| MIRA-S | | |
| Nor-propoxyphene | 429 | 70 |
| p-Hydroxypropoxyphene | 1,613 | 19 |
| Methandone | 1,049,000 | 0.03 |
| MIRA PLUS | | |
| Nor-propoxyphene | 383 | 77 |
| p-Hydroxypropoxyphene | 1,500 | 20 |
| Methadone | 1,185,800 | 0.03 |

What is claimed is:

1. A compound of formula:

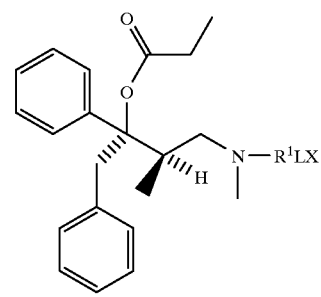

I wherein $R^1$ is a saturated or unsaturated straight or branched chain hydrocarbon of 1–15 carbon atoms;

L is a linker group through which X is bound and is selected from the group consisting of —(C=O)—, —NH—, —NR—, and a linker group containing up to 15 carbon atoms and up to 5 heteroatoms, provided, however, that L does not contain sulfur;

X is a labeling group or immunogenic carrier group.

2. The compound of claim 1 wherein X is a labeling group selected from the group consisting of a fluorophore, a chemilluminescent group, a radiolabeled group, an energy donor molecule, an energy acceptor molecule and an enzyme.

3. The compound of claim 1 wherein X is an immunogenic carrier material selected from the group consisting of a protein and a polypeptide.

4. The compound of claim 1 wherein L is a linking group of up to 15 carbon atoms and 5 heteroatoms, which heteratoms do not include sulfur.

5. The compound of claim 2 wherein X is fluorescein.

6. The compound of claim 3 wherein X is bovine serum albumin (BSA) or bovine thyroglobulin (BTG).

7. The compound of claim 4 wherein L is a linking group selected from the group consisting of aminomethyl benzoyl, aminobenzoyl, or a small polypeptidyl group.

8. A compound for use in an immunoassay comprising the compound of claim 1 wherein X is an immunogenic carrier, and which compound is bound to a microparticle.

9. The compound of claim 8 wherein the carrier material is a protein and the microparticle is a carboxylated latex microparticle.

10. The protein conjugate of formula:

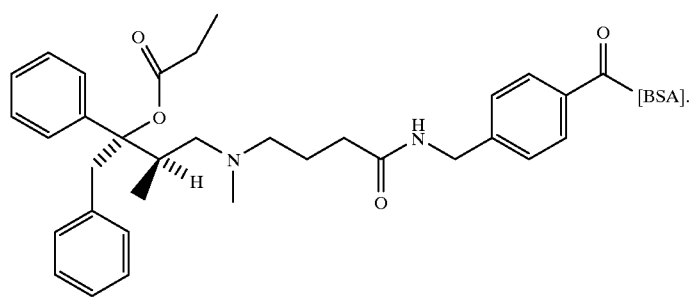

11. The immunogen of formula:

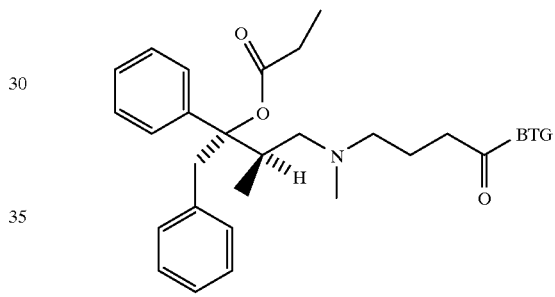

* * * * *